United States Patent

Varma et al.

Patent Number: 5,177,104
Date of Patent: Jan. 5, 1993

[54] 6-α-HYDROXY DERIVATIVES OF MEVINIC ACIDS

[75] Inventors: Ravi K. Varma, Belle Mead; Sam T. Chao, East Windsor; Eric M. Gordon, Pennington, all of N.J.

[73] Assignee: E. R. Squibb & Sons, Inc., Princeton, N.J.

[21] Appl. No.: 503,576

[22] Filed: Apr. 3, 1990

[51] Int. Cl.⁵ ............... A61K 31/365; C07D 309/30; C07C 69/74
[52] U.S. Cl. ................... 514/460; 514/824; 514/548; 549/292; 560/119
[58] Field of Search .......... 549/292; 560/119; 514/824, 460

[56] References Cited

U.S. PATENT DOCUMENTS

| | | | |
|---|---|---|---|
| 4,346,227 | 8/1982 | Terahara et al. | 560/119 |
| 4,410,629 | 10/1983 | Terahara et al. | 435/146 |
| 4,444,784 | 4/1984 | Hoffman et al. | 424/279 |
| 4,448,979 | 5/1984 | Terahara et al. | 549/292 |
| 4,450,171 | 5/1984 | Hoffman et al. | 424/279 |
| 4,868,210 | 9/1989 | Trivedi | 514/824 |

FOREIGN PATENT DOCUMENTS

| | | |
|---|---|---|
| 0065835 | 12/1982 | European Pat. Off. |
| 0137444 | 4/1985 | European Pat. Off. |
| 0306210 | 3/1989 | European Pat. Off. |
| 2075013A | 11/1981 | United Kingdom |

Primary Examiner—C. Warren Ivy
Assistant Examiner—Amelia A. Owens
Attorney, Agent, or Firm—Timothy J. Gaul

[57] ABSTRACT

Compounds of the formula

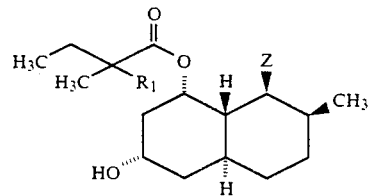

and pharmaceutically acceptable salts thereof have been found to possess activity as cell-selective HMG-CoA reductase inhibitors, thus making them useful as antihypercholesterolemic agents. In the above formula, Z is

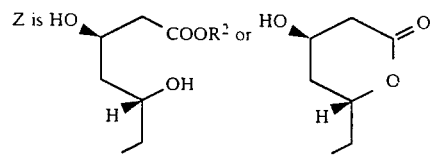

$R^1$ is hydrogen, alkyl, cycloalkyl, aryl or arylalkyl; and
$R^2$ is hydrogen, alkyl, ammonium, or alkali metal.

16 Claims, No Drawings

6-α-HYDROXY DERIVATIVES OF MEVINIC ACIDS

FIELD OF THE INVENTION

The present invention relates to 6-α-hydroxy mevinic acid derivatives, which are HMG-CoA reductase inhibitors useful as antihypercholesterolemic agents, and to methods of use for such compounds.

BRIEF DESCRIPTION OF THE INVENTION

In accordance with the present invention, compounds of the formula

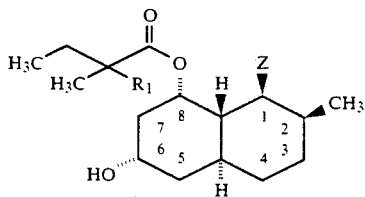

and pharmaceutically acceptable salts thereof have been found to possess activity as HMG-CoA reductase inhibitors, thus making such compounds useful as antihypercholesterolemic agents. In formula I and throughout this specification, the above symbols are defined as follows:

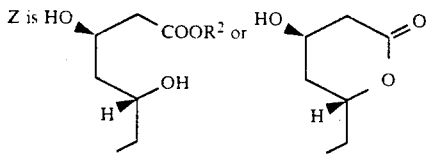

$R^1$ is hydrogen, alkyl, cycloalkyl, aryl or arylalkyl; and $R^2$ is hydrogen, alkyl, ammonium, or alkali metal (such as Na, Li, or K).

Novel processes for preparing Compound I and an intermediate thereof also form an integral part of this invention.

DETAILED DESCRIPTION OF THE INVENTION

Listed below are definitions of various terms used to describe this invention. These definitions apply to the terms as they are used throughout this specification (unless otherwise limited in specific instances) either individually or as part of a larger group.

The term "alkyl" or "alk" includes both straight and branched chain radicals of up to 12 carbons, preferably 1 to 8 carbons. Exemplary alkyl groups are methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. The term "alkyl" or "alk" also includes such groups having a halo-substituent, such as F, Br, Cl or I or $CF_3$, an alkoxy substituent, an aryl substituent, an alkyl-aryl substituent, a haloaryl substituent, a cycloalkyl substituent or an alkyl-cycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, wherein such groups may be substituted with 1 or 2 halogens, 1 or 2 lower alkyl groups and/or 1 or 2 lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl, wherein the substituent on either the phenyl or naphthyl may be 1 or 2 lower alkyl groups, 1 or 2 halogens (Cl, Br or F), and/or 1 or 2 lower alkoxy groups.

The term "halogen" or "halo" refers to fluorine, chlorine, bromine and iodine, as well as trifluoromethyl.

Preferred compounds of formula I are those wherein:
$R^1$ is hydrogen or alkyl (methyl most preferred);
Z is

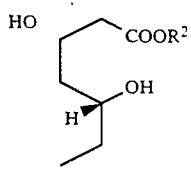

and
$R^2$ is hyd or alkali metal (lithium most preferred).

The compounds of formula I will be formulated with a pharmaceutical vehicle or diluent. The pharmaceutical composition can be formulated in a classical manner with solid or liquid vehicles or diluents and pharmaceutical additives appropriate to the desired mode of administration. The compounds can be administered by an oral route (e.g., tablets, capsules, granules or powders) or a parenteral route (e.g., injectable preparations).

A typical capsule for oral administration contains active ingredients (25 mg), lactose (75 mg) and magnesium stearate (15 mg). The mixture is passed through a 60-mesh sieve and packed into a No. 1 gelatin capsule.

A typical injectable preparation is produced by asceptically placing 25 mg of a water-soluble salt of sterile active ingredient into a vial, aseptically freeze-drying and sealing. For use, the contents of the vial are mixed with 2 ml of physiological saline, to produce an injectable preparation.

The compounds of the invention are inhibitors of 3-hydroxy-3-methylglutaryl coenzyme A (HMG-CoA) reductase and inhibit cholesterol biosynthesis. An important property of the compounds of the present invention is that they act more selectively in the cells of the target organ (liver) than in the cells of other organs or tissues.

Such compounds are useful in treating atherosclerosis to inhibit progression of disease, in treating hyperlipidemia to inhibit development of atherosclerosis, and in treating nephrotic hyperlipidemia. In addition, the compounds of the invention increase plasma high density lipoprotein cholesterol levels. As HMG-CoA reductase inhibitors, the compounds of the invention may also be useful in inhibiting formation of gallstones and in treating tumors.

The compounds of the present invention may also be employed in combination with antihyperlipoproteinemic agents, such as probucol, and/or with one or more serum cholesterol lowering agents such as Lopid ® (gemfibrozil), bile acid sequestrants such as cholestyramine, colestipol, DEAE-Sephadex ® as well as clofibrate, nicotinic acid and its derivatives, neomycin, p-aminosalicylic acid, lovastatin, pravastatin, visinolin (velostatin, symvastatin or sinvinolin) and the like, and/or one or more squalene synthetase inhibitors.

The above compounds to be employed in combination with the HMG-CoA reductase inhibitor of the invention will be used in amounts as indicated in the Physicians' Desk Reference (PDR).

The dose to be administered depends on the unitary dose, the symptoms, and the age and the body weight of the patient. A dose for adults is preferably between 20 and 2,000 mg per day, which can be administered in a single dose or in the form of individual divided doses from 1-4 times per day.

The compounds of this invention also have useful antifungal activities. For example, they may be used to control strains of Penicillium sp., *Aspergillus niger*, Cladosporium sp., *Cochliobolus miyabeorus* and *Helminthosporium cynodnotis*. For those utilities they are admixed with suitable formulating agents, powders, emulsifying agents or solvents (such as aqueous ethanol) and sprayed or dusted on the plants to be protected.

In addition, the compounds of the invention may also be useful in elevating HDL-cholesterol levels while lowering levels of LDL-cholesterol and serum triglycerides.

Compounds of formula I can be prepared by the following exemplary process.

Preparation of the compound

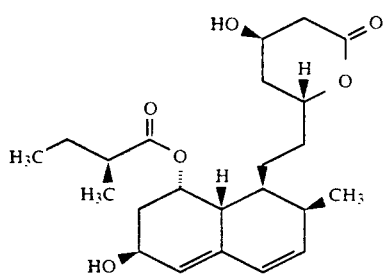

II is described in U.S. Pat. Nos. 3,983,140 and 4,346,227. In the process of forming compound I, compound II is placed in an inert solvent (e.g., tetrahydrofuran or dichloromethane) under an inert atmosphere (e.g., argon or nitrogen) at a temperature of about 15 to 25° C. and treated with an appropriate silyl protecting agent (e.g., t-butyldimethylsilyl chloride, triethylsilyl chloride, or phenyldimethylsilyl chloride) in the presence of an appropriate amine base (e.g., imidazole) to form

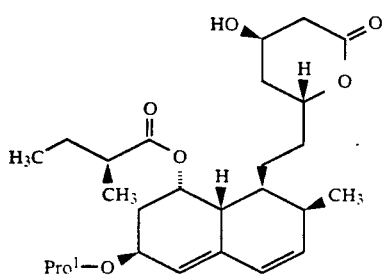

III where Pro$^1$ is a silyl oxygen-protecting group such as

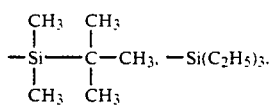

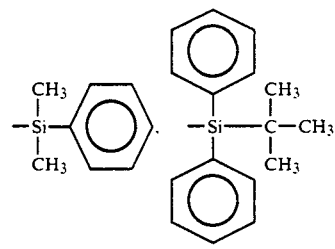

and the like.

Compound III is hydrogenated (e.g., with hydrogen gas) in an organic solvent (e.g., ethyl acetate) in the presence of a catalyst (e.g., platinum on carbon) to form a compound of the formula

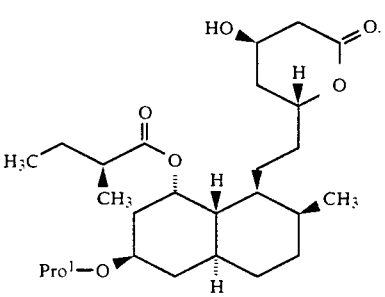

IV

Compound IV is treated with a base (e.g., potassium hydroxide) in a mixture of water and an organic solvent such as toluene (optionally containing some methanol) to form the potassium salt

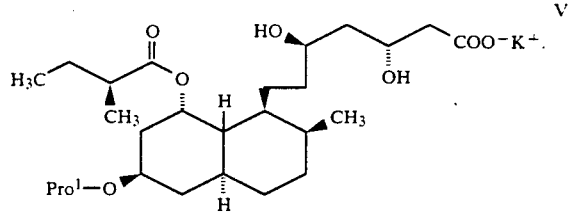

V

The potassium salt V is reacted in an organic solvent such as tetrahydrofuran with an organic base (e.g., pyrrolidine or piperidine) and n-butyllithium and an alkylating agent (e.g., iodomethane) in an inert atmosphere (e.g., argon) at about −60° to −20° C. The resulting amide product is acidified, isolated and heated to about 100–110° C. in an organic solvent (e.g., toluene) to form

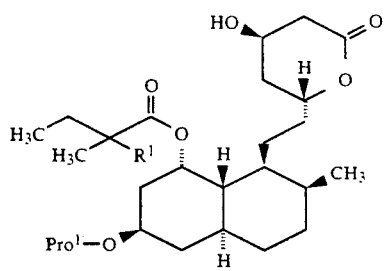

in which $R^1$ is methyl.

Compound VI is oxygen-protected by, for example, reaction with a protecting agent (e.g., benzyl bromomethyl ether) in the presence of an amine base (e.g., N,N-dimethylaniline) in an organic solvent (e.g., methylene chloride) to form

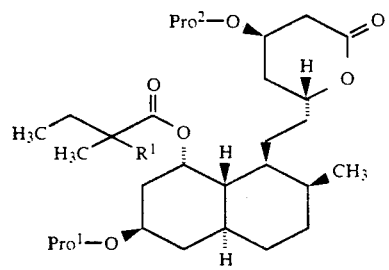

where $Pro^2$ is a different protecting group from $Pro^1$ and may be selected from benzyloxymethyl (which is preferred), paramethoxybenzyloxymethyl, tetrahydrylpyranyloxy, lower acyl and the like.

$Pro^1$ can then be removed by, for example, reaction with a deprotecting agent (e.g., hydrogen fluoride-pyridine) at about $-10$ to $10°$ C. under an inert atmosphere (e.g., nitrogen) in an inert solvent (e.g., acetonitrile) to form

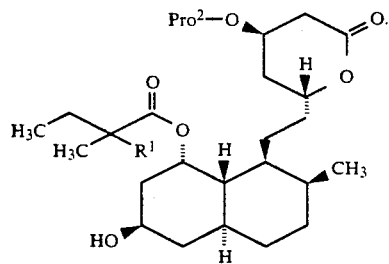

The isomeric configuration of the hydroxyl group in the 6-position is then changed by, for example, treatment with a weakly nucleophilic organic base and a sulfonic anhydride (e.g., trifluoromethane sulfonic anhydride) in an organic solvent (e.g., methylene chloride) at about $0°$ to $30°$ C. to form

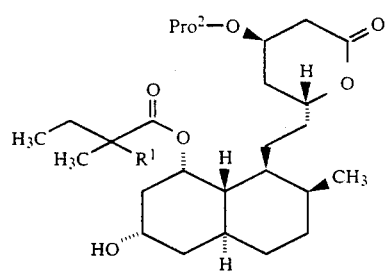

Examples of weakly nucleophilic organic bases are 2,6-lutidine (which is preferred), collidine, pyridine, quinoline, 2-methylquinoline, sodium bicarbonate, potassium bicarbonate, and the like.

$Pro^2$ is then deprotected (e.g., by hydrogen gas treatment) in an organic solvent (e.g., ethyl acetate) in the presence of a catalyst (e.g. palladium hydroxide on carbon) at about 20 to $30°$ to form Compound I wherein Z is the cyclized lactone

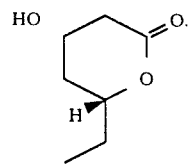

Alternatively, to form Compound I wherein $R^1$ is hydrogen, Compound III is (1) placed in a degassed suspension of a metal catalyst (e.g., platinum on carbon in an inert organic solvent (e.g., ethyl acetate of tetrahydrofuran), (2) subjected to hydrogen gas under a pressure of about 30 to 60 psi, and (3) oxygen-protected as described above (Compound VI→Compound VII) to form Compound VII wherein $R^1$ is hydrogen. Compound VII is also oxygen-deprotected as described above (Compound VII→Compound VIII) to give Compound VIII wherein $R^1$ is hydrogen. Compound VIII wherein $R^1$ is hydrogen can then be (1) reacted with a sulfonic anhydride as described above to give Compound IX wherein $R^1$ is hydrogen and (2) oxygen-deprotected to give Compound I wherein $R^1$ is hydrogen.

Compound I wherein Z is the lactone may be converted to the open-chain form by hydrolysis with an aqueous ammonium or alkali metal base (e.g., lithium hydroxide) at about 20 to $30°$ C. in an inert solvent (e.g., tetrahydrofuran). $R^2$ can be converted to hydrogen by treatment with a mild aqueous acid (e.g., potassium bisulfate).

The following working examples represent preferred embodiments of the invention. Unless otherwise specified, all temperatures are in degrees Celsius (°C.). The preparation of each compound appears below its name. As a shorthand reference, the compound prepared in part 1A will be called "Compound 1A" or "Intermediate 1A" and so forth for all compounds hereafter.

EXAMPLE 1

[1S-[1α,3α,4aα,7β,8β(2S*,4S*),8β]]-2,2-Dimethylbutanoic acid, decahydro-3-hydroxy-7-methyl-8-[2-[tetrahydro-4-hydroxy-6-oxo-2H-pyran-2-yl]ethyl]-1-naphthalenyl ester

1A. [1S-[1α(R*),3β,4β,7β,8β(2S*,4S*),8aβ]]-2-Methylbutanoic acid, 3-[[(1,1-dimethylethyl)dimethylsilyl]oxy]-1,2,3,7,8,8a-hexahydro-7-methyl-8-[2-(tetrahydro-4-hydroxy-6-oxo-2H-pyran-2-yl)ethyl]-1-naphthalenyl ester The starting material for preparation of intermediate A was [1S-[1α(R*),3β,4β,7β,8β(2S*, 4S*),8aβ]]-2-methylbutanoic acid, 3-hydroxy-1,2,3,7,8,8a-hexahydro-7-methyl-8-[2-(tetrahydro-4-hydroxy-6-oxo-2H-pyran-2-yl)ethyl]-1-naphthalenyl ester. Preparation of this starting material has been described in U.S. Pat. Nos. 3,983,140 and 4,346,227.

A solution of 8.43 g (20.7 mmol, 1.00 eq.) of the starting material in 80 ml of dry tetrahydrofuran under argon at ambient temperature was treated with 1.76 g (25.9 mmol, 1.25 eq.) of imidazole, followed by 3.44 g (22.8 mmol, 1.10 eq.) of t-butyldimethylsilyl chloride. A white precipitate formed almost immediately (5–10 sec). After stirring for 26 hours, the reaction mixture was diluted with 80 ml of ether, filtered and concentrated in vacuo. Purification of the residue by flash chromatography (with Merck silica gel; 40% ethyl acetate in hexanes) gave 7.41 g (a 69% yield) of the mono-silyated product (intermediate A) as a white solid, with a melting point of 111 to 115° C. (More typical yields for this conversion are in the range of 80 to 85%).

1B. [1S-[1α(R*),3β,4αα, 7β,8β(2S*,4S*), 8αβ]]-2-Methylbutanoic acid, 3-[[(1,1-dimethylethyl)dimethylsilyl]oxy]decahydro-7-methyl-8-[2-(tetrahydro-4-hydroxy-6-oxo-2H-pyran-2-yl)ethyl]-1-naphthalenyl ester To a degassed, argon-purged solution of 9.38 g, 18.0 mmol) of Compound 1A in 200 ml of ethyl acetate was added 1.4 g of 10% platinum on carbon. This suspension was subjected to 50 psi of $H_2$ in a Parr hydrogenation apparatus for 14.5 hours (overnight). Thin layer chromatography analysis indicated the complete consumption of starting material with generation of the desired product and some disilyated product. The filtered reaction mixture was concentrated and the products were isolated by flash chromatography. Elution with 45% hexanes in ethyl acetate gave 7.73 g (82%) of Compound 1B as a clear glass and elution with 30% hexanes in ethyl acetate gave 0.98 g (13%) of desilyated product.

1C. [1α,3β,4aα,7β,8β(2S*,4S*),8aβ]]-2,2-Dimethylbutanoic acid, 3-[[(1,1-dimethylethyl)dimethylsilyl]oxydecahydro-7-methyl-8-[2-(tetrahydro-4-hydroxy-6-oxo-2H-pyran-2-yl)ethyl]-1-naphthalenyl ester A solution of Compound 1B (10.5 g, 20.04 mmol) in a mixture of toluene (200 ml) and methanol (42 ml) was treated with 1.0 N potassium hydroxide (20 ml) at room temperature under an atmosphere of nitrogen for 45 minutes. The solvent was evaporated in vacuo to give a gum. This was azeotroped with benzene (250 ml) and then dried in vacuo at 45° (oil bath temperature) overnight to give a foamy solid.

To a chilled (−55°, acetonitrile-Dry ice bath) and stirred solution of the above solid in dry tetrahydron (150 ml) under an atmosphere of nitrogen was added dry pyrrolidine (6.48 ml, 77.63 mmol), followed by n-butyllithium (2.5 M in hexane, 27.84 ml, 69.6 mmol). The mixture was gradually warmed up to −25° (carbon tetrachloride-Dry ice bath) and stirred for 2.5 hours. Iodomethane (3.12 ml, 50.12 mmol) was added dropwise. After 1.0 hour, a small aliquot was worked up. $^1$H-NMR spectrum indicated there was 15–20% non-methylated starting material. Therefore, the mixture was recooled to −55°, more dry pyrrolidine (3.24 ml) and n-butyllithium (2.5 M in hexane, 13.92 ml) were added and the mixture was warmed up to −25°. After 2.5 hours, iodomethane (1.56 ml) was added and stirred for another hour. The resulting mixture was quenched with 10% potassium bisulfate solution (100 ml) at −25°, warmed up to room temperature, saturated with sodium chloride and extracted with ethyl acetate (3×100 ml). The combined ethyl acetate extracts were washed with a small amount of 5% sodium thiosulfate solution and brine, dried over anhydrous sodium sulfate and evaporated in vacuo to give a gummy residue (11.0 g).

The above gum was refluxed in dry toluene (200 ml) under an atmosphere of nitrogen for 4.0 hours. The solvent was then evaporated in vacuo to give a gummy material. This material was chromatographed on a column of silica gel (LPS-1, 450 g) eluting with ethyl acetate-hexane (1:3) to give 7.3g (67.5%) of Compound 1C as a gum with consistent $^1$H-NMR and $^{13}$C-NMR spectra.

1D. [1S-1α,3β,4aα,7β,8β(2S*,4S*),8aβ]]-2,2-Dimethylbutanoic acid, 3-[[1,1-dimethylethyl)dimethylsilyl]oxydecahydro-7-methyl-8-2-[tetrahydro-6-oxo-4-(phenylmethoxy)methoxy]-2H-pyran-2-yl]ethyl]-1-naphthalenyl ester To a chilled (0°, ice bath) and stirred solution of Compound 1C (7.3 g, 13.52 mmol) in dry dichloromethane (80 ml) under an atmosphere of nitrogen was added dry N,N-dimethylaniline (3.7 g, 30.53 mmol). After 15 minutes, benzyl bromomethyl ether (5.62 g, 26.13 mmol) was added. The resulting solution was gradually warmed up to room temperature and stirred for 20 hours. The solvent was partially removed in vacuo. Ethyl acetate (300 ml) was added. The ethyl acetate solution was washed with a 10% potassium bisulfate solution, a saturated sodium bicarbonate solution and brine, dried over anhydrous sodium sulfate and evaporated in vacuo to give an oil. This oil was chromatographed on a column of silica gel (LPS-1, 300 g) eluting with ethyl acetate-hexane (1:9) to give 8.5 g (95.4%) of Compound 1D as an oil with consistent $^1$H-NMR and $^{13}$C-NMR spectra

1E. [1S-[1α,3β,4aα,7β,8β(2S*,4S*),8aβ]]-2,2-Dimethylbutanoic acid, decahydro-3-hydroxy-7-methyl-8-[2-[tetrahydro-6-oxo-4-[(phenyl-methoxy)methoxy]-2H-pyran-2-yl]ethyl]-1-naphthalenyl ester A solution of Compound 1D (8.5 g, 12.9 mmol) in dry acetonitrile (100 ml) was cooled to 0° (ice bath) under an atmosphere of nitrogen and treated with two 4-ml portions of hydrogen fluoride-pyridine over 1.5 hours.

The reaction mixture was diluted with ethyl acetate (200 ml), washed with a 10% potassium hydrogen sulfate solution, brine and a dilute sodium bicarbonate solution, dried over anhydrous sodium sulfate and evaporated in vacuo to give a gum. This gum was chromatographed on a column of silica gel (Baker 60–200 mesh, 300 g), eluting with ethyl acetate-hexane (35:65 and 1:1) to give 6.0 g (85.4%) of Compound 1E as a solid (m.p. 73–77°) with consistent $^1$H-NMR and $^{13}$C-NMR spectra.

1F. [1S-[1α,3α,4aα,7β,8β(2S*, 4S*), 8aβ]]-2,2-Dimethylbutanoic acid, decahydro-3-hydroxy-methyl-8-[2-[tetrahydro-6-oxy-4-[(phenyl-methoxy) methoxy]-2H-pyran-2-yl]ethyl]-1-naphthalenyl ester To a chilled (ice bath) and stirred solution of Compound 1E (500 mg, 0.92 mmol) in dry dichloromethane (5 ml) under an atmosphere of nitrogen was added dropwise 2,6-lutidine (642 µl, 5.51 mmol), followed dropwise by trifluoromethane sulfonic anhydride (232 µl, 1.38 mmol). The mixture was stirred for 30 minutes, quenched with water (1.0 ml), warmed up to room temperature, diluted with a 10% potassium bisulfate solution (20 ml) and extracted with ethyl acetate (3×20 ml). The combined ethyl acetate extracts were washed with a 10% potassium bisulfate solution, a dilute sodium bicarbonate solution and brine, dried over anhydrous sodium sulfate and evaporated in vacuo to give a gum. This was chromatographed on a column of Merck Kieselgel-60 ® (150 g) eluting with ethyl acetate-hexanes (1:3 and 4:6) to give 245 mg (49%) of Compound 1F as a gum with consistent $^1$H-NMR and $^{13}$C-NMR spectra.

1G. [1S-[1α,3α,4aα,7β,8β(2S*,4S*), 8aβ]]-2,2-Dimethylbutanoic acid, decahydro-3-hydroxy-7-methyl-8-[2-[tetrahydro-4-hydroxy-oxo-2H-pyran-2-yl]ethyl]-1-naphthalenyl ester A slow stream of hydrogen was bubbled for 2.0 hours through a solution of Compound 1F (240 mg, 0.441 mmol) in ethyl acetate (6 ml) containing 20% palladium hydroxide on carbon (150 mg) at room temperature. The mixture was then filtered through a bed of celite ® and washed with a small amount of ethyl acetate. The filtrate and washings were combined and evaporated in vacuo to give a gum. This was chromatographed on a column of silica gel (Baker 60–200 mesh, 50g) eluting with acetate-hexanes (1:3) to give 145 mg (77.5%) of Example 1 as a solid with consistent $^1$H-NMR and $^{13}$C-NMR spectra.

EXAMPLE 2

[1S-[1α(βS*,ΔS*),2α,4aβ,6β,8β,8aα]]Decahydro-β, Δ,6-trihydroxy-2-methyl-8-(1,1-dimethylpropycarbonyloxy)-1-naphthalene heptanoic acid, monolithium salt A stirred solution of Example 1 (140 mg, 0.33 mmol) in tetrahydrofuran (3 ml) at room temperature under an atmosphere of nitrogen was treated with 1.0 N lithium hydroxide (660 µl, 0.66 mmol). After 30 minutes, the solvent was evaporated by a stream of nitrogen to leave a gummy residue. This residue was dissolved in water and chromatographed on a column of HP-20 (1.5"×1" column bed) eluting with deionized, distilled water (250 ml) and 50% methanol-water (250 ml) to give in the later eluate TLC-homogeneous Example 2. This eluate was evaporated in vacuo and lyophilized overnight to give 130 mg (87.9%) of a hydrated analytical specimen of Example 2 as a white solid with consistent IR, mass and $^1$H-NMR spectral data.

Anal. for $C_{24}H_{41}O_7Li \cdot 0.75\ H_2O$ (MW=462.04): Calc'd: C, 62.38, H, 9.27; Found: C, 62.41; H, 9.15.

IR Spectrum (KBr): µMax 3424, $Cm^{-1}$: (OH), 1715 $Cm^{-1}$ (C=O,ester), 1583 $Cm^{-1}$ (C=O, salt) etc.

Mass Spectrum: m/e $(m+Li)^+=469$, $(m-H)^-=461$, $(m+2Li-H)^+=655$, $(m+Li-2H)=467$, $(m+3Li-2H)^+=461$, $(m+2Li-3H)^-=453$, etc.

$H^1$-NMR Spectrum (270 mHz, $D_{20}$): δ6 0.77 (t+d,6H,$CH_3$), 1.00 (s,3H,$CH_3$), 1.02 (S,3H,$CH_3$), 2.28 (m,2H,$CH_2C$=O), 3.65 (m,1H,CH—OH), 4.04 (m,2H,CHOH+CHOH), and 5.08

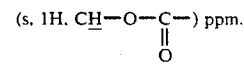

(s, 1H, CH—O—C—) ppm.

EXAMPLE 3

[1S-[1α,3β,4aα,7β,8β(2S*,4S*),8aβ]]-2-Methylbutanoic acid, decahydro-3-hydroxy-7-methyl-8-[2-(tetrahydro-4-hydroxy-6-oxo-2H-pyran-2-yl) ethyl]-1-naphthalenyl ester, partially racemized 3A. [1S-[1α(R*),3β,4aα,7β, 8β(2S*,4S*),8aβ]]-2-Methylbutanoic acid, 3-[[(1,1-dimethyl-ethyl)dimethylsilyl]oxy]decahydro-7-methyl-8-[2-(tetrahydro-4-hydroxy-6-oxo-2H-pyran-2-yl)ethyl]-1-naphthalenyl ester To a degassed, argon-purged solution of 9.38 g (18.0 mmol) of intermediate IA in 200 ml of ethyl acetate was added 1.4 g of 10% platinum on carbon. This suspension was subjected to 50 psi of $H_2$ in a Parr hydrogenation apparatus for 14.5 hours. Thin layer chromatography analysis indicated the complete consumption of intermediate 1A with generation of intermediate 3A and a by-product. The filtered reaction mixture was concentrated, and the products were isolated by flash chromatography. Elution with 45% hexanes in ethyl acetate gave 7.73 g (82%) of intermediate B as a clear glass.

3B. [1S-[1α(R*), 3β,4aα,7β,8β(2S*,4S*), 8aβ]]-2-Methylbutanoic acid, 3-[[(1,1-dimethylethyl)]oxy]decahydro-7-methyl-8-[2-[tetrahydro-6-oxo-4-[(phenylmethoxy)-methoxy]-2H-pyran-2-yl]ethyl]-1-naphthalenyl ester The generation of benzyloxymethyl bromide was carried out by bubbling hydrobromide through a methylene chloride solution of benzyloxymethyl chloride for 15 minutes at 0° C., followed by stirring at ambient temperature for 45 minutes and exhaustively stripping in vacuo all volatiles.

To a solution of 23.1 g (115 mmol, 2.42 eq) of benzyloxymethyl bromide in 40 ml of methylene chloride at 0° C. was added 15.6 ml (123 mmol, 2.60 eq) of N,N-dimethylaniline and a solution of 24.9 g (47.4 mmol, 1.0 eq) of intermediate 3A in 50 ml of methylene chloride. This mixture was brought immediately to ambient temperature and stirred for 18 hours. The reaction mixture was then diluted with 400 ml of ethyl acetate, washed sequentially with saturated aqueous copper sulfate (1×200 ml, 1×75 ml) and brine (1×150 ml), dried with magnesium sulfate and concentrated. The product was isolated by elution from silica gel with 10% ethyl acetate in hexanes, yielding 29.4 g (96.1%) of intermediate 3B as a clear, colorless, viscous oil.

3C.
[1S-[1α(R*),3β,4aα,7β,8β(2S*,4S*),8aβ]]-2-Methyl-
butanoic acid,
decahydro-3-hydroxy-7-methyl-8-[2-[tetrahydro-6-oxo-
4-[(phenylmethoxy)methoxy]-2H-pyran-2-yl]ethyl]-1-
naphthalenyl ester A solution of 28.8 g (44.7 mmol) of intermediate 3B in 400 ml of acetonitrile was cooled at −20° C. under argon and treated with three 10 ml portions of HF-pyridine over 2 hours, with warming to 0° C. after 1.5 hours. The reaction mixture was diluted with 500 ml of ethyl acetate and washed sequentially with saturated copper sulfate (aqueous 2×150 ml), brine (1×250, 200 and 150 ml) and saturated sodium bicarbonate (aqueous, 2×250 ml, 1×200 ml). After drying the ethyl acetate solution with sodium sulfate and concentrating, the crude product was purified by silica gel chromatography, eluting with 40% hexanes in ethyl acetate to yield 2.2 g (93.7%) of intermediate 3C as a clear, colorless oil.

[1S-[1α,3α,4aα,7β,8β(2S*,4S*),8aβ]]-2-Methyl-
butanoic acid,
decahydro-3-hydroxy-7-methyl-8-[2-[tetrahydro-6-oxo-
4-[(phenylmethoxy)
methoxy]-2H-pyran-2-yl]ethyl]-1-naphthalenyl ester,
partially racemized To a chilled (0° ice bath) and stirred solution of Compound 3C (3.78 g, 7.14 mmol) in dichloromethane (30 ml) under an atmosphere of nitrogen was added dropwise 2,6-lutidine (5.02 ml, 43.2 mmol). After 15 minutes, trifluoromethane sulfonic anhydride (1.78 ml, 10.7 mmol) was added dropwise. The mixture was stirred for 30 minutes, quenched with water (3 ml), warmed up to room temperature, diluted with a 10% potassium bisulfate solution (75 ml) and extracted with ethyl acetate (2×150 ml). The combined ethyl acetate extracts were washed with a 10% potassium bisulfate solution twice, a 5% sodium bicarbonate solution twice and brine, dried over anhydrous sodium sulfate and was evaporated in vacuo to give a gum. This was chromatographed on a column of Merck Kieselgel-60 ® (250 g), eluting with ethyl acetate-hexane (3:7 and 4:6) to give 1.25 g (33.1%) of thin-layer chromatography-homogeneous compound 3D as a gum, with consistent H1-NMR and C13-NMR spectra.

[1S-[1α,3α,4aα,7β,8β(2S*,4S*),8aβ]]-2-Methyl-
butanoic acid,
decahydro-3-hydroxy-7-methyl-8-[2-(tetrahydro-4-
hydroxy-6-oxo-2H-pyran-2-yl)ethyl]-1-naphthalenyl
ester, partially racemized A slow stream of hydrogen was bubbled through a solution of Compound 3D (100 mg, 0.188 mmol) in ethyl acetate (3 ml) containing 20% palladium hydroxide on carbon (50 mg) at room temperature for 1.0 hours, with monitoring of aliquots by thin-layer chromatography. It was then filtered through a bed of Celite ® and washed with a small amount of ethyl acetate. The filtrate and washings were combined and evaporated in vacuo to give a gum. This was chromatographed on a column of silica gel (15 g, Baker 60–200 mesh) eluting with ethyl acetate-dichloromethane (3:7) to give 68 mg (87.9%) of thin-layer chromatography homogeneous Example 3 as a gum with consistent H1-NMR and C13-NMR spectra Another run using 120 mg of Compound 3D gave 82 mg more of Example 3.

EXAMPLE 4
[1S-[1α(βS*,ΔdS*),2α,4αβ,6β,8β,8aα]]-Decahydro-
β,Δ,6-trihydroxy-2-methyl-8-(1-methylpropylcar-
bonyloxy)-1-naphthaleneheptanoic acid, monolithium
salt A stirred solution of Example 3 (135 mg, 0.329 mmol) in tetrahydrofuran (4 ml) at room temperature under an atmosphere of nitrogen was treated with 1.0 N lithium hydroxide (411 ml, 0.411 mmol). After 1.0 hour, the solvent was evaporated by a stream of nitrogen to give a gum. This gum was dissolved in water and chromatographed on a column of HP-20 (1.5″×1.0″ column bed) eluting with deionized, distilled water (about 250 ml) and 50% methanol-water (about 250 ml) to give in the later eluate thin-layer chromatography-homogeneous Example 4. This eluate was evaporated in vacuo and lyophilized overnight to give 110 mg (77%) of a hydrated analytical specimen of Example 4 as a white solid with consistent IR, mass and H1-NMR spectral data.

Anal. for $C_{23}H_{39}O_7Li \cdot 0.3\ H_2O$ (MW:434.50+0.3 $H_2O$):
Calc'd: C, 62.80; H, 9.07;
Found: C, 62.71; H, 9.10;
IR Spectrum (KBr): $\mu$Max 3424 $Cm^{-1}$ (OH), 1718 and 1707 $Cm^{-1}$ (C=O,ester), 1583 $Cm^{-1}$ (C=O,acid salt), etc.
Mass Spectrum: m/e (m-H)$^-$=427, (m+Li)$^+$=635, (m+Li−2H)$^-$=633, (m−2Li−H)$^+$=661, etc.
H1-NMR Spectrum (270 MHz, $D_2O$): δ0.75 (d,3H,J=7.0,$CH_3$), 0.81, 0.82 (2t,3H,J=~7.6,$CH_3$), 1.05 (d,3H,J=~7.0,$CH_3$), 3.65 (m,1H,CH—OH), 4.05 (m,2H,CHOH+CH+OH), 5.07

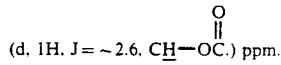

We claim:
1. A compound of the formula

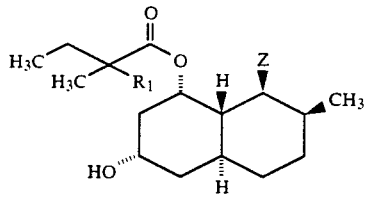

and pharmaceutically acceptable salts thereof, wherein

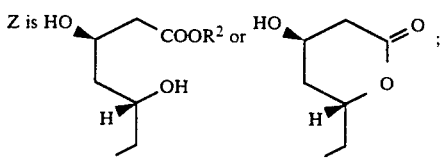

$R_1$ is hydrogen, alkyl, cycloalkyl, aryl or arylalkyl;
$R^2$ is hydrogen, alkyl, ammonium, or alkali metal;
"alkyl" refers to straight and branched chain groups of up to twelve carbons;

"cycloalkyl" refers to cyclic hydrocarbon groups of three to twelve carbons; and "aryl" refers to monocyclic or bicyclic aromatic hydrocarbon groups of six to ten carbons.

2. The compound of claim 1, wherein $R^1$ is hydrogen or alkyl.

3. The compound of claim 1, wherein $R^1$ is methyl.

4. The compound of claim 1, wherein Z is

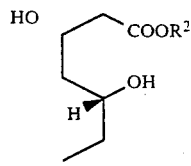

and $R^2$ is hydrogen or alkali metal.

5. The compound of claim 1, wherein Z is

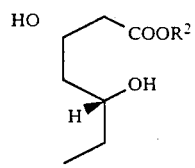

and $R^2$ is lithium.

6. The compounds of claim 1 having the names:

[1S-[1α,3α,4aα,7β,8β(2S*,4S*),8β]]-2,2-Dimethylbutanoic acid, decahydro-3-hydroxy-7-methyl-8-[2-[tetrahydro-4-hydroxy-6-oxo-2H-pyran-2-yl]ethyl]-1-naphthalenyl ester;

[1S-[1α(βS*,ΔS*),2α,4αβ,6β,8β,8αβ]]-Decahydro-β,Δ, 6-trihydroxy-2-methyl-8-(1-methylpropylcarbonyloxy)-1-naphthaleneheptanoic acid, monolithium salt;

[1S-[1α,3α,4aα, 7β,8β(2S*,4S*),8aβ]]-2-Methylbutanoic acid, decahydro-3-hydroxy-7-methyl-8-[2-(tetrahydro-4-hydroxy-6-oxo-2H-pyran-2-yl)-ethyl]-1-naphthalenyl ester, partially racemized; and

[1S-[1α(βS*, ΔS*),2α,4αβ,6β,8β,8αα]]-Decahydro-β,Δ,6-trihydroxy-2methyl-8-(2-dimethyl-1-oxobutoxy)-1-naphthaleneheptanoic acid, monolithium salt.

7. A hypocholesterolemic or hypolipidemic composition comprising a compound as defined in claim 1 and a pharmaceutically acceptable carrier therefor.

8. A process for preparing a compound of the formula

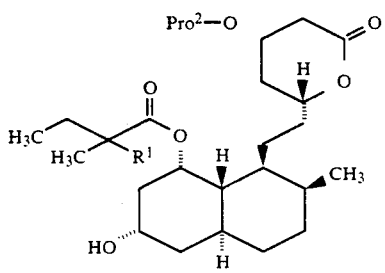

which comprises treating a compound of the formula

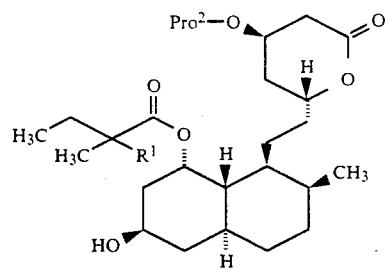

with a base selected from 2,6-lutidine, collidine, pyridine, quinoline, 2-methylquinoline, sodium bicarbonate and potassium bicarbonate and sulfonic anhydride, wherein:

$R^1$ is hydrogen, alkyl cycloalkyl, aryl, or arylalkyl; and $Pro^2$ is a protecting group.

9. The process of claim 8, wherein the base is 2,6-lutidine.

10. The process of claim 8, wherein the protecting group is benzyloxymethyl.

11. A process for preparing a product of the formula

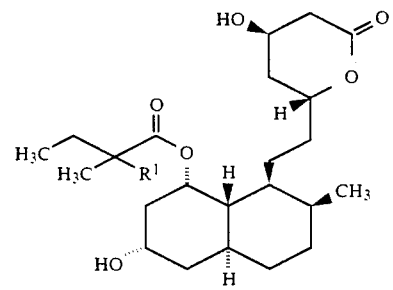

which comprises:

(a) treating a compound of the formula

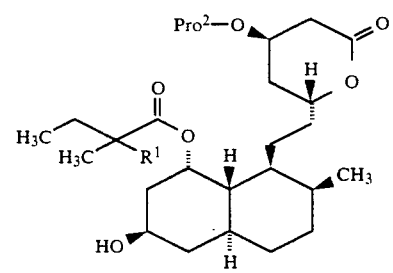

wherein $Pro^2$ is a protecting group with a base selected from 2,6-lutidine, collidine, pyridine, quinoline, 2-methylquinoline, sodium bicarbonate and potassium bicarbonate and a sulfonic anhydride to form an alpha-hydroxy intermediate of the formula

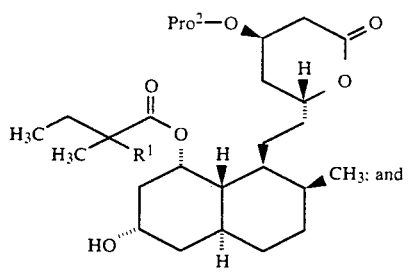

(b) deprotecting the alpha-hydroxy intermediate in the presence of a catalyst to form the product;

wherein $R^1$ is hydrogen, alkyl, cycloalkyl, aryl or arylalkyl.

12. The process of claim 11, wherein the base is 2,6-lutidine.

13. The process of claim 11, wherein $Pro^2$ is benzyloxymethyl.

14. A process for preparing a product of the formula

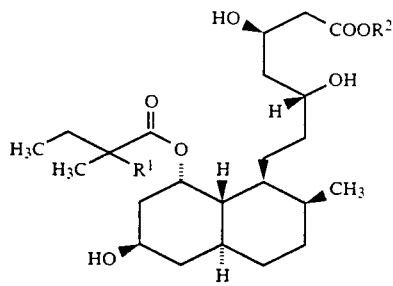

which comprises:

(a) treating a compound of the formula

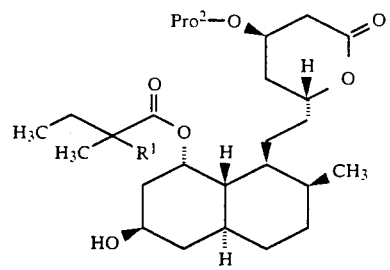

wherein $Pro^2$ is a protecting group with an organic base selected from 2,6-lutidine, collidine, pyridine, quinoline, 2-methylquinoline, sodium bicarbonate and potassium bicarbonate, and a sulfonic anhydride to form an alpha-hydroxy intermediate of the formula

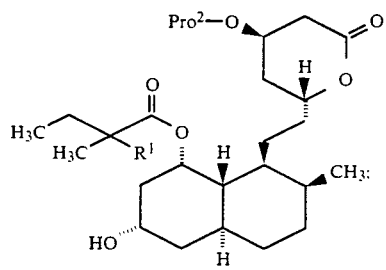

(b) deprotecting the alpha-hydroxy intermediate in the presence of a catalyst to form a lactone of the formula

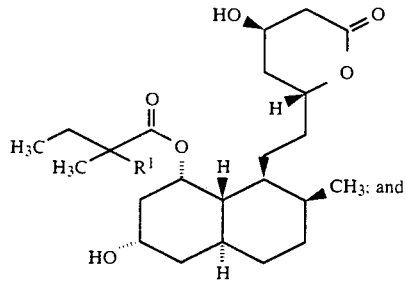

(c) hydrolyzing the lactone with an aqueous ammonium or alkali metal base to form the product; wherein:
 $R^1$ is hydrogen, alkyl, cycloalkyl, aryl or arylalkyl; and
 $R^2$ is hydrogen, alkyl, ammonium, or alkali metal.

15. The process of claim 14, wherein the organic base is 2,6-lutidine.

16. The process of claim 14, wherein $Pro^2$ is benzyloxymethyl.

* * * * *